(12) United States Patent
Good et al.

(10) Patent No.: US 6,194,224 B1
(45) Date of Patent: Feb. 27, 2001

(54) DIAGNOSTIC MEMBRANE CONTAINING FATTY ACID SARCOSINATE SURFACTANT FOR TESTING ORAL FLUID

(75) Inventors: Carl M. Good, Groton, MA (US); Shirley Smith, Key Biscayne, FL (US)

(73) Assignee: Avitar, Inc., Canton, MA (US)

( * ) Notice: Subject to any disclaimer, the term of this patent is extended or adjusted under 35 U.S.C. 154(b) by 0 days.

(21) Appl. No.: 09/123,376

(22) Filed: Jul. 27, 1998

(Under 37 CFR 1.47)

(51) Int. Cl.$^7$ .......................... C12Q 1/28; G01N 33/543; G01N 21/78; G01N 33/00
(52) U.S. Cl. ..................... 436/518; 436/514; 436/8; 436/86; 436/568; 436/805; 436/810; 436/169; 436/174; 436/175; 435/5; 435/11; 435/7.92; 435/28; 435/4; 435/514; 435/8; 435/86; 435/287.1; 435/568; 435/287.2; 435/287.7; 435/287.8; 435/805; 435/810; 435/962; 422/56; 422/57; 422/58; 422/61; 128/771
(58) Field of Search .................... 128/771; 435/5, 435/11, 7.92, 28, 4, 287.1, 287.2, 287.7, 287.8, 805, 810, 962, 970; 436/514, 8, 86, 568, 169, 174, 175, 805, 810, 518; 422/56, 57, 58, 61

(56) References Cited

U.S. PATENT DOCUMENTS

| 5,112,758 | | 5/1992 | Fellman et al. | 436/8 |
|---|---|---|---|---|
| 5,124,266 | * | 6/1992 | Coryn et al. | 436/86 |
| 5,609,160 | | 3/1997 | Bahl et al. | 128/771 |
| 5,639,626 | | 6/1997 | Kiaei et al. | 435/7.92 |
| 5,656,503 | | 8/1997 | May et al. | 436/514 |
| 5,695,930 | | 12/1997 | Weinstein et al. | 435/5 |
| 5,695,947 | | 12/1997 | Guo et al. | 435/11 |
| 5,728,587 | * | 3/1998 | Kang et al. | 436/518 |
| 5,811,254 | * | 9/1998 | Wu | 435/28 |
| 5,821,073 | | 10/1998 | Lee | 435/7.92 |
| 5,874,216 | | 2/1999 | Mapes | 435/6 |

* cited by examiner

Primary Examiner—Rodney P. Swartz
Assistant Examiner—Lisa Daniels-Cook
(74) Attorney, Agent, or Firm—George W. Neuner; Dike, Bronstein, Roberts & Cushman LLP

(57) ABSTRACT

A diagnostic test strip for determining the presence of a specified analyte in a fluid sample is described. The test strip has a test membrane sandwiched between two layers of a plastic sheath. The upper layer of the sheath has a sample well into which a liquid sample is placed. The test membrane has a sample receiving zone typically containing a buffer and a fatty acid sarcosinate. Adjacent to the sample receiving zone is a reagent zone containing reagent chemicals including gold colloid particles coated with antibodies to the specified analyte. In fluid connection with the reagent zone is a test zone containing immobilized molecules of the specified analyte. Preferably, in fluid connection with the test zone is a control zone containing an indicator that changes color when wetted by the sample and a liquid sink zone to absorb excess liquid in the sample.

11 Claims, 3 Drawing Sheets

US 6,194,224 B1

DIAGNOSTIC MEMBRANE CONTAINING FATTY ACID SARCOSINATE SURFACTANT FOR TESTING ORAL FLUID

FIELD OF THE INVENTION

The present invention is related to devices for the diagnostic testing of specimen, e.g., oral fluid, urine, or the like. The device of the present invention provides a test membrane containing a fatty acid sarcosinate surfactant structured and adapted for rapid testing of specimen for any of a variety of analytes, such as HIV, Hepatitis B, Hepatitis C, etc., and for use in drug testing, pregnancy testing, and the like.

BACKGROUND OF THE INVENTION

Analytical devices suitable for use in the home, clinic or doctor's office, which are intended to give an analytical result that is rapid and requires a minimum degree of skill and involvement from the user are well known. Such test devices are common, for example, in home pregnancy tests and blood glucose tests.

Typically, a diagnostic strip is provided that contains reagent chemistry that forms a color or other indication of the presence of the analyte in a sample. The strip is read visually or by a meter.

Many rapid diagnostic tests use a process known as solid phase immunoassay immunochromatography. In a typical process, a sample is deposited on a paper strip and is moved by capillary action from one end to the other. The sample dissolves or solubilizes dried chemical reagents and immunologic reagents attached to particles such as colloidal gold. The suspension of colloidal gold particles moves across the paper strip by capillary action. The colloidal gold typically has antibodies, coated thereon or attached thereto, that bind with the test drug. A band of immobilized drug is provided. When colloidal gold particles move into this band, if antibodies have not bound with some test drug present in the specimen, the particles will bind with the drug immobilized in the band region and a color will be produced. If drug from the specimen sample has bound to the antibody, then the colloidal particles will migrate through the band region without forming a color product. Typically, such tests are complete in about five to ten minutes.

U.S. Pat. No. 5,656,503 describes a test device useful in pregnancy testing. A hollow casing is constructed of moisture-impervious solid material, such as a plastic, and contains a dry porous carrier, which communicates indirectly with the exterior of the casing via a bibulous sample receiving member that protrudes from the casing. The test sample is applied to the receiving member and permeates therefrom to the porous carrier. The porous carrier contains a first zone having a labelled specific binding reagent that is freely mobile within the carrier when in a moist state. The mobility is facilitated by a sugar in an amount effective to reduce interaction between the test strip and the labelled reagent. The carrier also has a second zone, spatially distinct from the first zone, containing an unlabelled specific binding reagent for the same analyte, which is permanently immobilized on the carrier and, therefore, is not mobile in the moist state. The two zones are arranged such that the liquid sample can permeate first into the first zone and then into the second zone. An aperture is provided in the casing to observe the extent to which labelled reagent becomes bound in the second zone.

U.S. Pat. No. 5,609,160 describes a collection device and package including a reagent strip having a testing portion that contains an absorbent cotton pad. The pad may be placed in the mouth to collect an oral fluid sample. A plastic frame surrounds the pad to help hold the fluid thereon. The testing strip contains at its opposite end a sealing mechanism for sealing engagement with a preservative pouch, and an oversized handle with a patient identifying mechanism. The preservative pouch contains a pair of seals. The first seal, located proximately to the user, enables a preservative that is maintained within the pouch to be sealed during shipment of the pouch to the user. Thereafter, the user punctures the first seal upon placement of the reagent pad into the pouch. The sealing mechanism contained on the reagent pad then seals the at the opening in the pouch to maintain the reagent pad in sealing engagement with the pouch. At its distal end, the pouch contains a second sealing mechanism. This sealing mechanism helps to protect the preservative as well as the oral sample within the pouch during shipment from the user to a testing laboratory. A chemical that will change color when sufficient oral fluid is taken up by the pad is coated on the pad.

Amperometric assay is another approach to the rapid assay of analytes in biological fluids. Such assays use electrodes to sense the presence of a redox mediator in the sample by various enzyme catalyzed reactions. U.S. Pat. No. 5,695,947 describes a device or biosensor for determining the presence of cholesterol in a sample. The cholesterol biosensor comprises a sensing electrode having a redox mediator dispersed in an electrically conductive graphite formulation, a reference electrode such as a standard silver—silver chloride or calomel electrode, and a membrane reagent strip containing reagents and enzymes with the strip in simultaneous contact with electrically conductive medium having the redox mediator dispersed therein and the reference electrode. The reagent strip has a second redox mediator system. An opening is provided to place a sample on the reagent strip. The liquid in the sample permeates the reagent strip to provide electrical connection between the reference electrode and the conductive medium.

Test membranes can exhibit problems of accuracy and repeatability of test results when the specimen sample is a viscous fluid, such as saliva. In such cases, the sample may not flow uniformly through the membrane to the testing zone. Thus, the visual detection may show uneven coloration. This can be difficult to interpret, even with a meter because the meter reading may differ depending upon the area of focus by the optics. In an electrochemical device, non-uniform concentrations can provide a conductive path that is not representative of the sample.

Thus, new and better diagnostic test membranes are desired, particularly for uniform and consistent results in economical rapid diagnostic testing.

SUMMARY OF THE INVENTION

We have discovered that liquid flow through a diagnostic test membrane can be made surprisingly more uniform when a fatty acid sarcosinate surfactant is provided in the sample receiving zone of the test membrane, particularly when the fluid is a viscous fluid, such as saliva. In accord with the present invention, a diagnostic test membrane comprises a bibulous matrix that has a sample receiving zone for receiving a liquid specimen suspected of containing a particular analyte, reagent chemistry and spaced from the sample receiving zone a detection zone for detecting the presence of said particular analyte, the sample moving between the sample receiving zone and the detection zone, wherein the sample receiving zone contains a fatty acid sarcosinate surfactant. Preferably, the fatty acid has from about 10 to about 18 carbon atoms and more preferably is a saturated fatty acid.

In a preferred embodiment of the invention, a diagnostic test membrane comprises a porous membrane having a sample receiving zone containing a fatty sarcosinate surfactant, reagent chemistry including antibodies to a particular analyte that are freely mobile when the membrane is moist, and spaced from the sample receiving zone a detection zone for detecting the presence of said particular analyte, the detection zone containing immobilized molecules of said particular analyte that are not free to move when the membrane is moist. A detectable change is produced in the detection zone when antibodies bind to the immobilized analyte. Preferably the detectable change is a visible change, such as production of a color. Also preferably, a control zone is provided downstream of the detection zone, wherein the presence of the sample causes a detectable change, preferably a visible change. The detection of change in the control zone can denote the presence of sufficient sample in the diagnostic test membrane. A liquid sink zone can also be provided further downstream from the control zone, e.g., at an opposite end of the diagnostic test membrane from the sample receiving zone. Of course, the zones can also be constructed in annular rings around the sample receiving zone.

The porous membrane is preferably contained between two non-porous layers having an aperture in one of the membranes for placing a sample of the specimen on the sample receiving zone, and preferably having a visually open aperture adjacent to the detection zone and the control zone for visual observation of a detectable change therein.

Surprisingly, the use of a fatty acid sarcosinate surfactant has been found to provide better flow characteristics of a specimen, particularly saliva, in the test strip and improved appearance of a detectable color change provided by the reagent chemistry, which can provide increased accuracy and repeatability of results.

Additional diagnostic membrane structures within the scope of the present invention will be apparent to those skilled in the art upon consideration of the more detailed description of the invention and preferred embodiments which follow.

DETAILED DESCRIPTION OF THE INVENTION INCLUDING PREFERRED EMBODIMENTS

The invention will be described in detail with reference to the drawings, which illustrate a preferred embodiment of the invention. As discussed above, the present invention provides a diagnostic test membrane comprising a bibulous matrix that has a sample receiving zone for receiving a liquid specimen suspected of containing a particular analyte, reagent chemistry and spaced from the sample receiving zone a detection zone for detecting the presence of said particular analyte.

Figure 1:
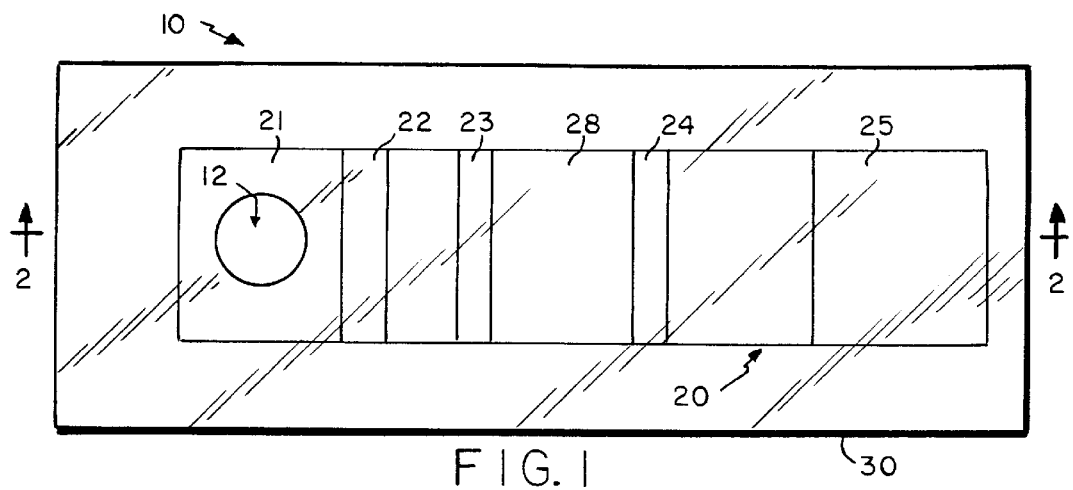
FIG. 1 is plan view of a diagnostic test device in accord with a preferred embodiment of the invention.

FIG. 1 illustrates a diagnostic test device 10 comprising a test membrane 20 sandwiched in a plastic sheath 30. The test device has a sample well 12 into which a liquid sample is placed onto a sample receiving zone 21 that contains a buffer and a fatty acid sarcosinate in a pad made of a non-woven fibrous material. The sample is absorbed by the pad, solubilizes the buffer and fatty acid sarcosinate, and migrates to an adjacent reagent zone 22 containing reagent chemicals in fibrous matrix. The reagent chemicals include gold colloid particles coated with antibodies to the particular analyte for which this test strip is designed to detect. The liquid sample mobilizes the gold colloid particles and continues to migrate with the colloid particles toward an into a test zone 23, which contains molecules of the analyte immobilized on a microporous nitrocellulose membrane. The pores of the microporous nitrocellulose membrane are preferably in a range of from about 0.2 to about $0.5\mu$ in diameter. The sample continues to migrate to a control zone 24, which contains an immobilized antibody to the antibody coated on the colloidal gold particles (i.e., an anti-antibody) that indicates when wetted by the sample containing gold particles with analyte bound to the antibodies that thus have not bound to the immobilized analyte in the test zone, also on the microporous nitrocellulose membrane. A liquid sink zone 25 (or waste pad) made of a fibrous material is provided to absorb excess liquid in the sample.

The plastic sheath consists of an upper layer 31 and a lower layer 32, both of which can be made from any plastic material to provide a means for handling the test strip and viewing it without touching the sample. The upper layer 31 is made of an opaque plastic and has an aperture to provide the sample well 12. A window 33, preferably open, is located in the upper layer to visualize a change in the test zone and/or the control zone caused by the presence of a sample. The lower layer 32 also can be a colored plastic material. For example, a white lower layer can enhance the reflection of light through some bibulous materials for reading a visible color change in the test zone 23 and the control zone 24.

The diagnostic test device 10 is made by assembling the components as follows. The lower plastic layer 32 of the sheath 30 is cut to size and placed on a support. A strip about 1.5 inches long and 0.5 inch wide has been found to be satisfactory. However, the size may be varied depending upon the application, type of handling (manual or mechanical), and other variables.

Figure 2:
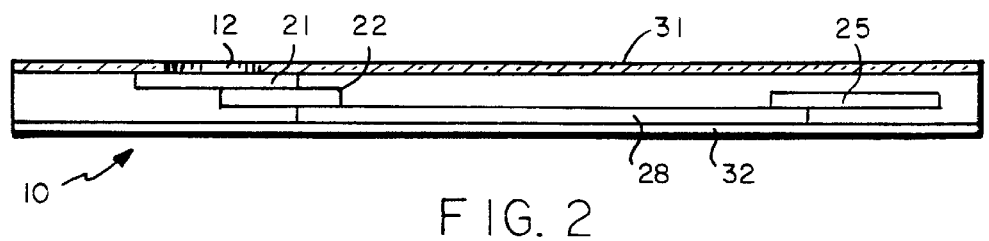
FIG. 2 is a sectional view taken at line 2—2 of FIG. 1.
Figure 3:
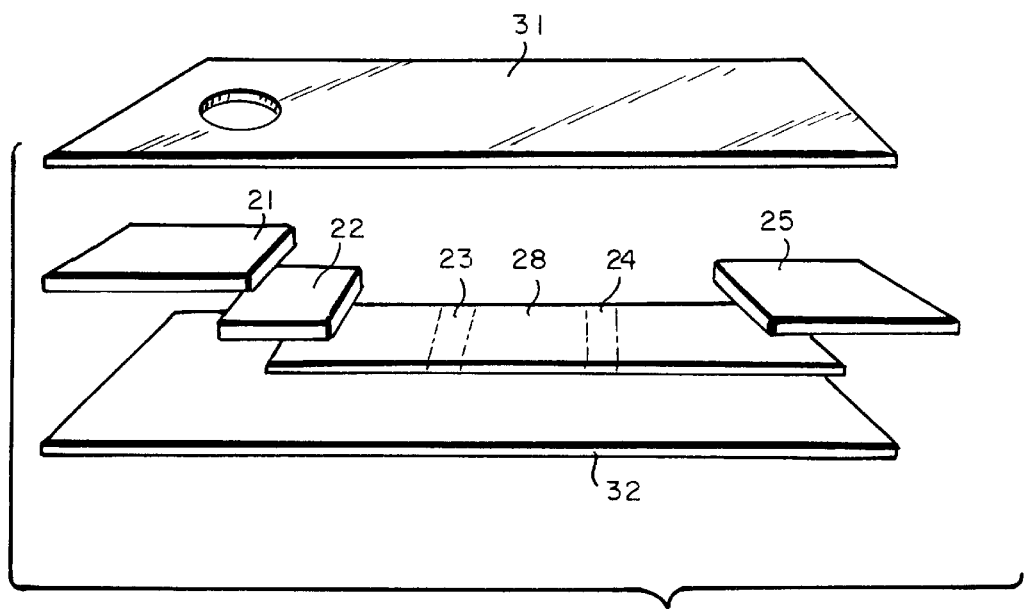
FIG. 3 is an exploded view of the test device of FIG. 1.

The microporous nitrocellulose layer is coated with stripes of suitable chemicals to provide the test zone 23 and control zone 24. A layer of solution containing the appropriate chemicals is coated in the surface of the nitrocellulose in a stripe to form each zone. By controlling the amount of solution laid down, the width of the zones can be controlled with a suitable distance between the zones being devoid of chemicals. The coated layer is then dried, cut into the desired size and positioned on top of plastic layer 32 as illustrated in FIGS. 2 and 3. Any suitable membrane material can be used, for example, a $0.5\mu$ nitrocellulose microporous filter membrane.

The reagent zone 22 is made by imbibing reagent chemicals into a fibrous polyvinyl or polyester filter layer to provide the appropriate concentration and drying the layer. Any suitable filter material can be used, for example, a 1.2μ hydrophilized polypropylene filter material (SA3J853F0) sold by Millipore Corporation (Bedford, Massachusetts). After drying the reagents, the membrane is cut into the desired size and positioned on the nitrocellulose membrane as illustrated in FIGS. 2 and 3.

The sample receiving zone 21 is made by imbibing a solution containing a suitable buffer and a fatty acid sarcosinate into a sheet of non-woven material to provide the appropriate concentration. The buffer is selected for the analyte and specimen for which the test strip is designed. A preferred fatty acid sarcosinate is sodium myristoyl sarcosinate, which is provided at a concentration of about 1.0 wt %. The fatty acid sarcosinate surfactant can be obtained from Hampshire Chemical Corporation, which manufactures and sells such surfactants under the brand name Hamposyl. The surfactant sold as Hamposyl M30 is sodium myristoyl sarcosinate. Preferably, the fatty acid sarcosinate is present in the imbibing solution at a concentration of from about 0.1% to about 10% by weight. The sheet is dried, cut into the desired size and positioned adjacent the reagent zone 22 as illustrated in FIGS. 2 and 3. The non-woven material can be, for example, any conventional filter material such as 470 paper (Cat. No. 539929) or 740 paper (Cat. No. 539930), which are available from Schleicher and Schuell.

Now the upper layer 31 of sheath 30 can be positioned over the assembled components so that the aperture 12 is above the sample receiving zone 21. The upper and lower layers of sheath 30 are sealed at their edges by heat sealing the plastic of by use of an adhesive material. Preferably, upper layer 31 and lower layer 32 are separated from the test layers comprising the test zone, control zone, reagent zone, sample receiving zone, etc. by ridges integrally attached to the upper 31 and lower 32 layers to avoid wicking of the sample along the contact surfaces.

In accord with the embodiment illustrated in the drawings, the bibulous matrix consists of separate components. The bibulous matrix can be any of a variety of materials having a porous structure for absorption of aqueous fluids, for example, non-woven fibrous materials including paper and microporous polymer membranes including foam membranes.

Another preferred bibulous material is a polyurethane foam membrane. Preferably, heat and pressure are applied to at least one surface of the polyurethane foam to enhance its use as a diagnostic membrane. The treated surface can absorb fluid more readily, maintain a greater attraction for the fluid as compared to the untreated foam membrane, and provide for a linear flow of fluid at the surface through capillary action. Suitable reagents can be applied to zones on the surface of the treated foam membrane for detecting a particular analyte in a diagnostic test.

Before treatment, the open cell polyurethane foam material preferably has an average cell size of approximately 0.005 inch to about 0.02 inch in diameter. The thickness of the foam material is preferably about 0.1 to about 0.125 inch. This material is treated with temperature and pressure to permanently partially collapse the cell structure such that the surface of the foam is provided with small cells or pores and/or reticulated formations. The characteristics of the surface will vary depending upon the particular temperature and pressure used. These characteristics can range from cells that are not completely collapsed or fused and, in general, have an average cell size, for example, of about 0.005 inch in diameter to a treated surface wherein the cells are virtually eliminated leaving a reticulated structure. The altered structure continues for a measurable depth into the base foam material. The depth can range preferably from about 0.001 inch to about one-half of the thickness of the base material, more preferably from about 0.01 to about 0.02 inch. The greater density in the treated area has been found to promote capillary flow through the modified structure. The treated area appears to retain fluid and only when it has become overly saturated does it expel fluid into the less absorbent macrocellular area of the foam membrane. Thus, the macrocellular layer becomes a reservoir for excess fluid.

The cells are collapsed preferably by heating the polyurethane foam to a temperature near its softening point, which can range from about 300° F. to about 450° F. depending upon the pressure used. Pressures ranging from about 5 psi to about 120 psi can be used, more preferably 60 psi. The particular temperature and pressure to obtain the desired result can be found by routine experimentation. Both sides of the base material can be treated utilizing heated rollers or platens; however, treating one side is sufficient for use as a diagnostic membrane. Silicon coated release paper or coatings on the rollers or platens can be used for ease of processing.

The foam base can be made of a variety of absorbent foams. Other materials for the foam member include, for example, polyurethane foam, polyethylene foam, polyvinylchloride foam, ethylvinylacetate foam, polyethylene/ethylvinylacetate foam, polyester foam and polyether foam. Absorbent Porex™, silicone and latex foams can also be used. A particularly useful foam for use with a saliva specimen is a polyurethane foam sold under the mark HYDRASORB® by Avitar, Inc., Canton, Mass.

The preferred polyurethane foam has a uniform cell count of about 60 or more cells per linear inch. More preferably, the uniform cell count is about 80 to 120 cells per linear inch.

Typical materials used for the plastic sheath are, for example, polyethylene, polypropylene, polyester, polyethylene terephthalate, polyvinyl chloride, or the like.

Chemical reagent systems are well known for detecting a wide variety of analytes. Any such reagent systems can be used in the test membrane of the present invention.

In one preferred embodiment of the present invention for an immunoassay diagnostic test strip, the sample receiving zone 21 is a mixed cellulose ester (MCE) filter material containing 10 $mg/cm^2$ sodium myristoyl sarcosinate and 10 $mg/cm^2$ retained in the test zone. When an adequate amount of the drug is present, it will fill all of the limited antibody binding sites. That will prevent binding of the colloidal gold particles in the test zone because no antibody can bind to the immobilized drug. Therefore, a positive sample will inhibit the formation of a visible line in the test zone region of the strip. A reference or control zone with a secondary antibody is located downstream of the test zone region. A visible control line should appear in this control region to indicate that sample is present. Normally, a negative oral fluids sample will produce two colored lines, one in the test zone region and one in the control zone region and a positive oral fluids sample will show only one line in the control zone region. If the test strip has been stressed and the anti-analyte antibodies on the colloidal gold are damaged or if the anti-anti analyte antibodies in the control zone are damaged, then the control zone will not become colored indicating a no test condition requiring additional testing with other test strips.

An amperometric assay can be used with the test strip of the present invention by placing suitable electrodes across the membrane in the detection zone.

Figure 4:
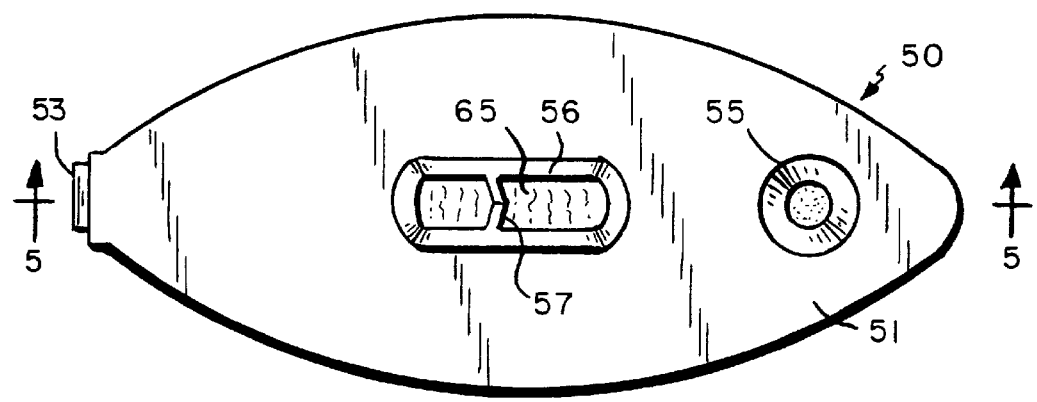
FIG. 4 is a plan view of a preferred diagnostic test device in accord with the present invention.
Figure 5:
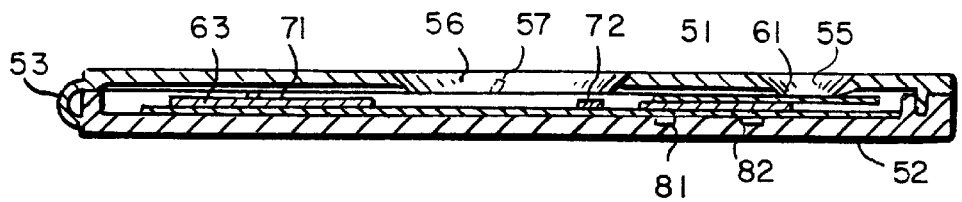
FIG. 5 is a cross sectional view taken at line 5—5 of FIG. 4.

Another test device structure of the present invention is illustrated in FIGS. 4–8. As illustrated, the diagnostic test device 50 consists of a plastic casing having an integrally molded plastic upper layer 51 and a plastic lower layer 52 joined by a plastic hinge. The upper layer 51 has a sample receiving well 55 and a viewing aperture 56. A bridging member 57 divides the viewing aperture into two regions. In FIG. 4, the test zone region is on the left side of the bridging member 57 and the control zone region is on the right side.

Figure 6:
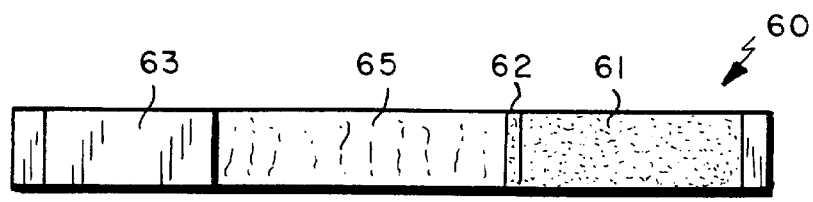
FIG. 6 is a plan view of the diagnostic test strip contained in the diagnostic test device of FIG. 4.
Figure 7:
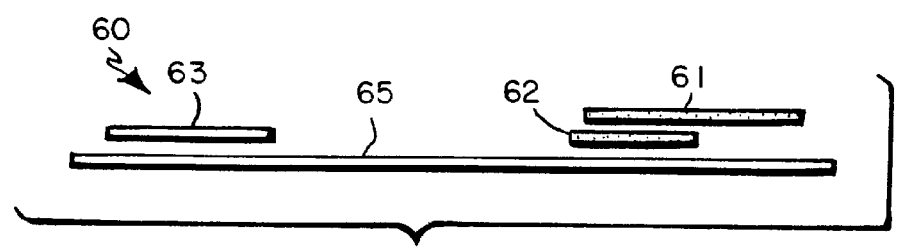
FIG. 7 is an exploded side view of the test strip of FIG. 6.

Inside the diagnostic test device 50 is a diagnostic test strip 60, which is illustrated in more detail in FIGS. 6 and 7. The test strip is built up of components, which include a sample receiving layer, a chemical reagent layer 62, a test results layer 65 and an excess sample sink layer 63. In this embodiment, the test results layer also provides a carrier layer for the assembly of the other layers into the test strip. The layers preferably are bound together by an adhesive in a manner that does not interfere with fluid flow between the layers.

Figure 8:
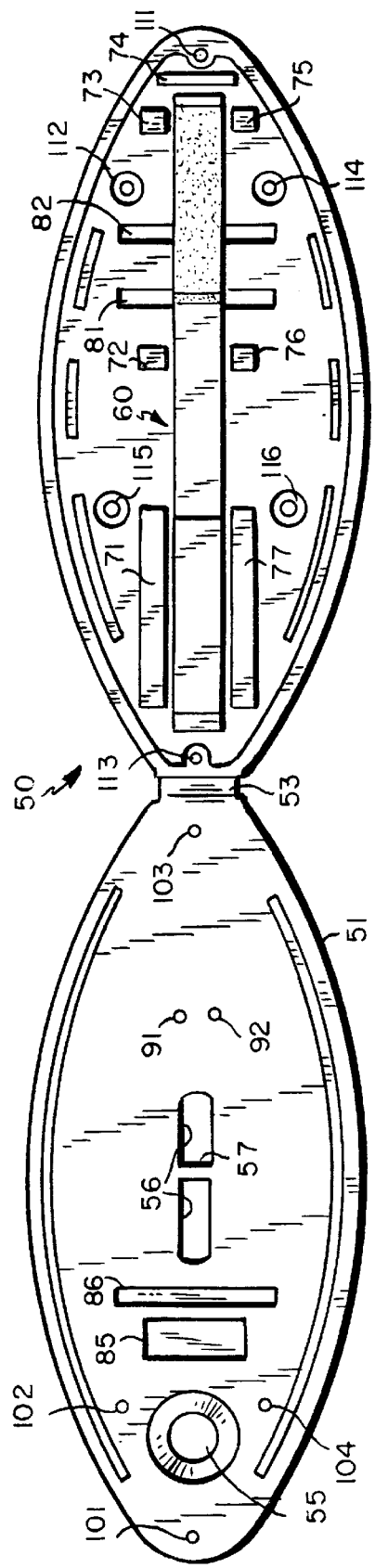
FIG. 8 is a plan view of the opened diagnostic test device of FIG. 4.

The test strip 60 is positioned within the plastic casing of the test device 50, as illustrated in FIG. 8. Conveniently, the lower layer of the plastic casing has integral ribs or islands 71–77 to position the test strip with respect to the sample receiving well 55, the viewing aperture 56 and the bridging member 57. Preferably, channels 81 and 82 are provided in the lower layer 52 and channels 85 and 86 are provided in the upper layer 51 of the casing to avoid wicking of liquid sample along the surface in contact with the test strip. The sample receiving well is constructed to contact the test strip for additional positioning stability. Also, pins 91 and 92 are integrally formed in the upper layer to contact the test strip for additional positioning stability when the casing is closed. Preferably, integral posts 101–104 in the upper layer 51 are received in integral post receptacles 111–114 to hold the casing closed. Additional integral columns 115 and 116 are provided with the posts 101–104 and receptacles 111–114 to support the upper layer 51 in spaced relationship with the lower layer 52. Reagents are coated on the test results layer 65 (as described with respect to FIG. 3) so that results appear appropriately in the viewing aperture 56.

The invention has been described in detail with reference to preferred embodiments thereof. However, it will be appreciated that, upon consideration of the present specification and drawings, those skilled in the art may make modifications and improvements within the spirit and scope of this invention as defined by the claims. For example, reagent chemistry that forms colored changes in the test zone and/or control zone can also be used. Such reagent chemistries are well known to those skilled in the diagnostic test strip art.

We claim:

1. A diagnostic test strip comprising a bibulous matrix having:

a sample receiving zone for receiving a liquid specimen of oral fluid suspected of containing a particular analyte, reagent chemistry located for contact with the sample for detecting the particular analyte, and spaced from the sample receiving zone in a sample migration direction a detection zone for determining the presence of said particular analyte by providing a detectable change observable in the detection zone, wherein the sample migrates between the sample receiving zone and the detection zone, and wherein the sample receiving zone contains a sodium myristol sarcosinate surfactant.

2. The diagnostic test strip according to claim 1, wherein the bibulous material comprises a microporous membrane.

3. The diagnostic test strip according to claim 1, wherein the reagent chemistry includes antibodies to said particular analyte that are freely mobile when the test strip is moist, and the detection zone contains immobilized molecules of said particular analyte that are not free to move when the test strip is moist.

4. The diagnostic test strip according to claim 1, further comprising a control zone downstream of the detection zone, wherein the presence of the sample causes a detectable change.

5. The diagnostic test strip according to claim 1, further comprising a liquid sink zone to absorb excess sample.

6. The diagnostic test strip according to claim 1, further comprising a liquid sink zone at an opposite end of the diagnostic test membrane from the sample receiving zone.

7. The diagnostic test strip according to claim 1, wherein the bibulous material comprises as separate components, each of which is in fluid contact with each other, a sample receiving zone, a reagent chemistry zone, and a detection zone.

8. The diagnostic test strip according to claim 7, wherein the bibulous material further comprises a separate liquid sink zone.

9. The diagnostic test strip according to claim 7, wherein the bibulous material further comprises a separate control zone.

10. The diagnostic test strip according to claim 7, wherein the bibulous material comprises an open cell, polyurethane foam membrane that is heat and pressure treated to provide at least one surface that can absorb fluid more readily than untreated polyurethane foam.

11. The diagnostic test strip of claim 1, wherein the oral fluid comprises saliva.

* * * * *